United States Patent
Collier et al.

(10) Patent No.: US 7,686,830 B2
(45) Date of Patent: Mar. 30, 2010

(54) SUTURE ANCHORING DEVICE

(75) Inventors: John Collier, Franklin Lakes, NJ (US);
Robert Nering, Sergeantsville, NJ (US);
Irene Nozad, Branchburg, NJ (US);
Etan Chatlynne, Brooklyn, NY (US)

(73) Assignee: Ethicon, Inc., Somerville, NJ (US)

( * ) Notice: Subject to any disclaimer, the term of this patent is extended or adjusted under 35 U.S.C. 154(b) by 1127 days.

(21) Appl. No.: 10/743,667

(22) Filed: Dec. 22, 2003

(65) Prior Publication Data
US 2005/0149120 A1  Jul. 7, 2005

(51) Int. Cl.
A61B 17/10 (2006.01)
A61B 17/04 (2006.01)
F16G 11/00 (2006.01)
F16L 3/00 (2006.01)

(52) U.S. Cl. ........................ 606/232; 606/139; 606/233; 24/129 R; 24/130; 24/115 N

(58) Field of Classification Search ................. 606/139, 606/232, 233, 148; 24/115 R, 129 R, 130, 24/132 R, 136 R, 115 N; 289/13, 14
See application file for complete search history.

(56) References Cited

U.S. PATENT DOCUMENTS

| | | | |
|---|---|---|---|
| 1,830,014 A | 3/1931 | Brady | |
| 2,075,508 A | 3/1937 | Davidson | |
| 2,458,252 A | 1/1949 | Chatterton | |
| 3,409,014 A | 11/1968 | Shannon | |
| 3,910,281 A * | 10/1975 | Kletschka et al. | ........... 606/232 |
| 4,291,698 A * | 9/1981 | Fuchs et al. | .................. 606/232 |
| 4,823,794 A * | 4/1989 | Pierce | ........................ 606/232 |
| 4,939,820 A | 7/1990 | Babcock | |
| 5,474,572 A | 12/1995 | Hayhurst | |
| 5,645,553 A | 7/1997 | Kolesa et al. | |
| 6,066,160 A | 5/2000 | Colvin et al. | |
| 6,106,545 A | 8/2000 | Egan | |
| 6,152,935 A * | 11/2000 | Kammerer et al. | .......... 606/144 |
| 6,165,204 A | 12/2000 | Levinson et al. | |
| 6,432,123 B2 | 8/2002 | Schwartz et al. | |
| 6,599,311 B1 * | 7/2003 | Biggs et al. | .................. 606/232 |
| 2004/0260344 A1 * | 12/2004 | Lyons et al. | ................. 606/232 |
| 2005/0096699 A1 * | 5/2005 | Wixey et al. | ................. 606/232 |

* cited by examiner

*Primary Examiner*—(Jackie) Tan-Uyen T. Ho
*Assistant Examiner*—Melissa Ryckman
(74) *Attorney, Agent, or Firm*—Roberts Mlotkowski Safran & Cole, P.C.

(57) ABSTRACT

A suture anchoring device comprising (1) a first retaining member having a first surface, a second surface and a first outer edge; where the second surface lies in a first plane; the first retaining member having an opening that extends from the first outer edge to at least partially through the second surface to an inner point of the first retaining member; (2) a second retaining member having a third surface, a fourth surface and a second outer edge; where the third surface lies in a second plane, the second retaining member having a holding means; and (3) a coupler having a third outer edge and a cross-sectional area taken in a plane parallel to the first plane that is smaller than the cross-sectional area of the first retaining member taken in a plane parallel to the first plane; where the coupler joins the first retaining member to the second retaining member at the second surface and third surface; wherein the second and third surfaces are parallel to each other and non-coterminous.

22 Claims, 2 Drawing Sheets

SUTURE ANCHORING DEVICE

FIELD OF THE INVENTION

The present invention relates to a suture anchoring and tensioning device for use with sutures in surgical procedures. More particularly, the present invention pertains to an anchoring device that maintains the tension that is set by the surgeon in at least one suture in order to anchor and restrict movement of the suture at the surgical site.

BACKGROUND OF THE INVENTION

In surgical procedures, sutures are commonly used to close incisions and to reunite damaged tissue. Typically, the sutures are maneuvered and passed through the affected tissue and the free ends of the sutures are individually tied together by the surgeon. In some surgical procedures, the surgical site area is sufficiently exposed to permit the surgeon to access and tie the suture manually with a surgical knot. In other surgical procedures, such as endoscopic procedures, laparoscopic procedures, arthroscopic procedures and the like, or when robotic surgical procedures occur, the surgical site is inaccessible to the surgeon's hands. As a result, the surgeon must tie each of the suture ends into a knot at a location remote from the surgical site, and then manipulate suitably configured instruments for sliding the surgical knot to the site of the incision. Further, surgeons may tie surgical knots intracorporeally (inside of the body) using surgical tools to tie the knot down to the tissue. In general, suture knot tying is cumbersome and is one of the more time-consuming steps in the suturing process of the surgical procedure. In the foregoing circumstances, it is desirable to replace knot tying during surgical procedures in order to significantly reduce the duration of surgical operations with a device or method that is simple for the surgeon to utilize. This is especially true with regard to minimally invasive surgical procedures where the tying of surgical knots within confined spaces is extremely difficult and time consuming.

Additionally, it is noted that knots create weak points in a suture. That is to say, when a failure load is applied to a knotted suture, assuming the suture is otherwise free from imperfections, the suture will break at the knot. Therefore, elimination of surgical knots in the suture would also eliminate the weak stress points created in the suture by the surgical knot.

Suture locking and suture anchoring devices such as suture clips, surgical fasteners, hinged clips, suture terminating devices, hemostatic clips, and suture fixation devices of various configurations, designs, structures, and materials of construction are well known in the prior art. For example, U.S. Pat. No. 2,075,508 discloses a suture retainer whereby a suture may be fixed relative to a surgical button. The suture is received and wedged between the button and a clamping plate in order to securely clamp the suture. There are a number of shortcomings to this retainer. First, due to the suture manipulation required to use this retainer, a laparoscopic applicator device would be extremely difficult to produce profitably. Furthermore, the wedging and clamping action will induce stress concentrations in the suture, which likely lead to reduced failure loads.

U.S. Pat. No. 6,066,160 to Colvin, et al. discloses a suture terminator device for use in minimally invasive surgery. The suture terminator device includes a pair of locking apertures with teeth for engaging a portion of a suture at the locking apertures' threaded ends. Not only does this device require laparoscopically guiding two strands of suture between two very small apertures, it also requires that the sutures be squeezed tightly by these teethed apertures, thereby diminishing the integrity of the suture and significantly reducing the maximum tension the suture can withstand.

U.S. Pat. No. 6,106,545 to Egan discloses a suture tensioning and fixation device, which includes a retaining element for frictionally engaging a suture that may subsequently be melted to bond to the suture for a permanent fixation. This melting and bonding action will compromise the integrity of the suture and therefore, because suture strength is of utmost concern in most surgeries, this method of fixation of the retaining element to the suture is not suitable for most surgeries.

U.S. Pat. No. 5,474,572 to Hayhurst and U.S. Pat. No. 5,645,553 to Kolesa et al. disclose the use of a hinged clip that snaps closed after the suture threads are placed within the holding members. The hinge clip is snapped into place such that the suture is held transversely across the holding members, thus locking the suture in place. There is a possibility of improperly actuating or inadvertently releasing the snap, which could lead to an insecure fixation of the suture. In addition, weak stress points are created where the suture is held within the clip.

In view of the deficiencies of the prior art discussed hereinabove, there remains a need for a suture anchoring device that is simple to use, particularly during laparoscopic surgery, in order to eliminate manual knot tying by the surgeon performing the surgical procedure, while not compromising the integrity of the suture.

Another object of the present invention is to provide a suture anchoring device that is at least as strong as conventional surgical knots.

Another object of the present invention is to provide a suture anchoring device that is easy and cost effective to manufacture in bulk.

Another object of the present invention is provide a suture anchoring device that is suitable for a wide variety of sutures (i.e., such as monofilament and braided sutures).

SUMMARY OF THE INVENTION

The present invention provides a suture anchoring device that is comprised in part of a first retaining member having a first surface, a second surface and a first outer edge that is connected via a coupler in a parallel, non-coplanar fashion to a second retaining member having a third surface, a fourth surface and a second outer edge. The first retaining member has an opening that extends from the first outer edge to at least partially through the second surface to an inner point of the first retaining member, and the second retaining member has a holding means. When used in a surgical procedure, the suture is introduced into the device, the device is positioned atop the wound site, and the suture is introduced into the opening in the first retaining member, wrapped around the coupler and held in place via the holding means in the second retaining member.

DETAILED DESCRIPTION OF THE INVENTION

The suture anchoring device described herein can be used in combination with multiple sutures or with a single suture for various types of surgical procedures by surgeons. The suture anchoring device may be fabricated from any biocompatible medical material, such as polymeric or metallic. The polymeric material may be absorbable within a mammalian body (e.g. polydioxanone such as poly(1,4-dioxan-2-one), polymers or copolymers of organic hydroxyesters, polyglycolide, polylactide, polyhydroxy butyric acid, polycaprolactone, polytrimethylene carbonate and polyvinyl alcohol), or it may be non-absorbable (e.g. polyolefins such as polyethylene or polypropylene, polyesters, fluorpolymers such as polytetrafluoroethylene, polyamides such as nylon, and combinations thereof). Furthermore, the suture anchoring device may be fabricated via standard machining processes, injection molding, or a lithographic process (e.g. stereolithography).

Figure 1:
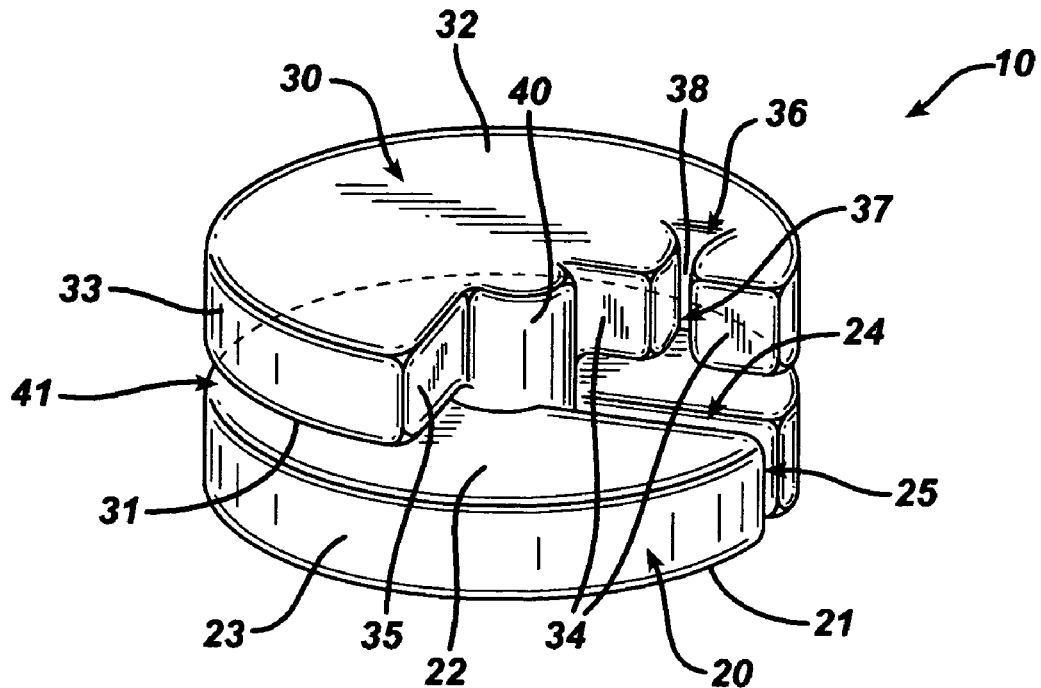
FIG. 1 is a perspective view of a suture anchoring device constructed in accordance with an embodiment of the present invention, the device being shown in a configuration comprised of two disk-like retaining members.

Referring to FIG. 1, there is shown a suture anchoring device 10 for use in surgical procedures for anchoring and tensioning sutures. The suture anchoring device may be comprised in part of a first retaining member 20 having a first surface 21, a second surface 22 and a first outer edge 23 that is connected in a parallel, non-coplanar fashion to a second retaining member 30 having a third surface 31, a fourth surface 32 and a second outer edge 33. The cross sectional area of the first retaining member taken in a plane parallel to the second surface may be substantially the same as, greater or less than the cross sectional area of the second retaining member taken in a parallel plane. First retaining member 20 is connected to the second retaining member 30 by a coupler 40. First retaining member 20 contains a first opening 24 that may extend from the entrance 25 located at the first outer edge 23 to any point within the first retaining member up to the coupler 40, and/or from the first surface 21 to the second surface 22, while the second retaining member has a holding means for securing the suture in place. Furthermore, the second surface 22 and third surface 31 of retaining members 20 and 30 form the boundaries of a space 41 that resides between the two retaining members and about the coupler 40. The width of this space is preferably as large as the diameter of the suture that is to be secured within the suture anchoring device. In one embodiment, second retaining member 30 may be comprised of a disk-like structure having one sector absent. In this embodiment, second retaining member 30 is also comprised of a fifth surface 34 and a sixth surface 35 that lie nominally perpendicular to the third 31 and fourth 32 surfaces. A holding means, comprised of a second opening 36, originates on the fifth surface 34 and ends at a point within the second retaining member. The span of the entrance 37 of second opening 36 is less than the width of the rear wall 38 of second opening 36. The width of second opening 36 is approximately the same size as the suture that is to be secured. In an alternate embodiment, a plane that coincides with the fifth surface 34 passes through the first opening 25 of the first retaining member 20.

In another embodiment, the holding means may be comprised in part of a hook member upon fifth surface 34 in lieu of or in addition to second opening 36 to provide further stability to the portion of the excess suture immediately adjacent to the wrapped portion of the suture.

Preferably, the corners and edges of the suture anchoring device are rounded in order to minimize the possibility of damaging the suture during application of the device and to maximize the holding strength the device provides. Particularly, all edges and corners of the device are rounded to prevent any sharp portions of device from cutting or pinching suture in a manner that will compromise its strength or integrity.

Figure 2:
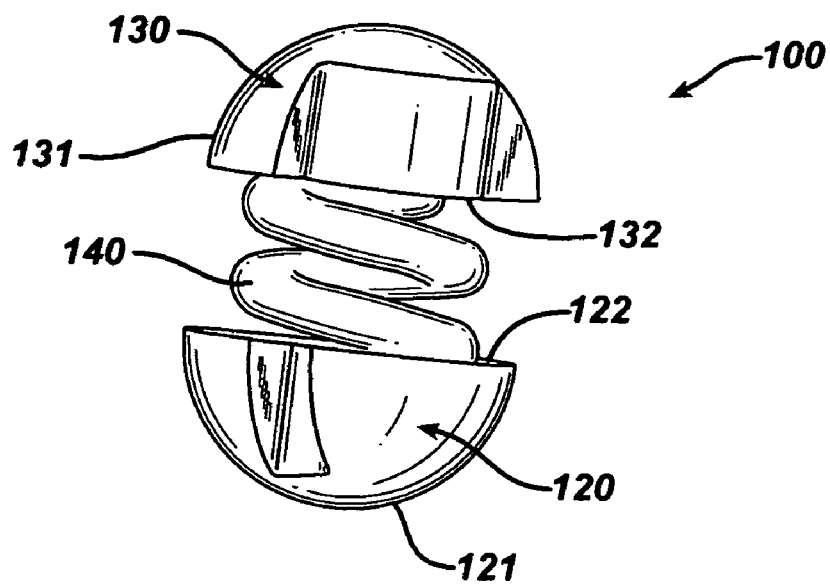
FIG. 2 is a perspective view of a suture anchoring device constructed in accordance with another embodiment, the device being shown in a configuration comprised of two dome-like retaining members and of a helical coupler.

Referring to FIG. 2, another embodiment of a suture locking device 100 is shown. This embodiment may be comprised in part of a first retaining member 120 having a first surface 121 and a second surface 122 that is connected in a parallel, non-coplanar fashion to a second retaining member 130 having a third surface 131 and a fourth surface 132. First retaining member 120 is connected to second retaining member 130 by a coupler 140. Coupler 140 may have a cylindrical cross section, such as a shaft, or a helical shape in order to provide a tortuous path for the suture as the suture is wound around the coupler. This tortuous path provides additional friction between the coupler and the suture to aid in stronger suture fixation.

Figure 3A:
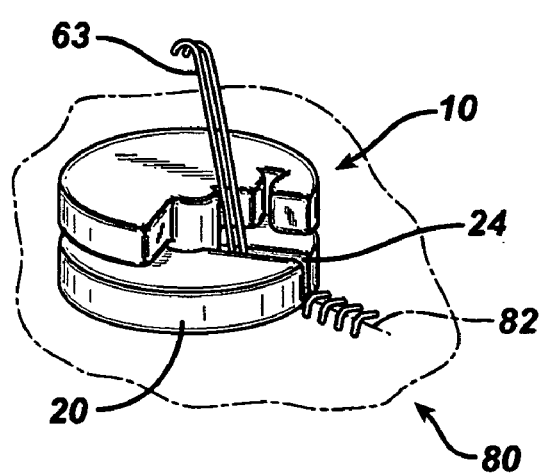
FIGS. 3a to 3d are schematic representations which illustrate the steps involved in the attachment of a suture to the suture anchoring device of FIG. 1.
Figure 3B:
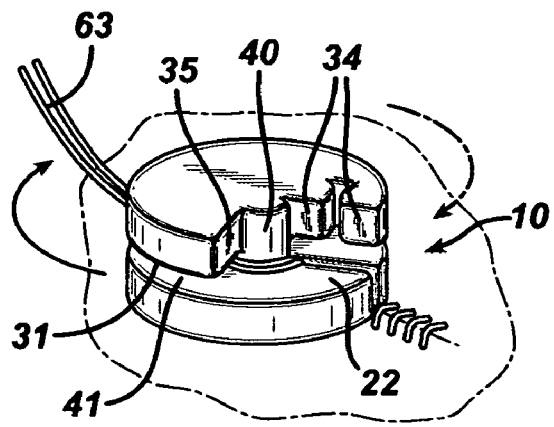
Figure 3C:
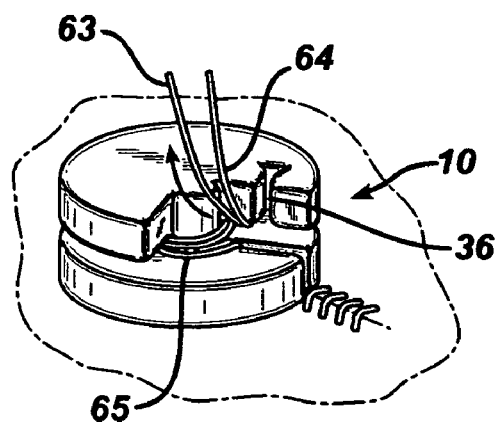
Figure 3D:
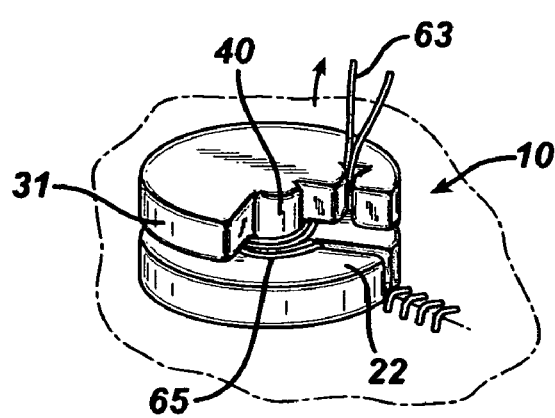

Reference made herein to a suture may include one or more sutures. The suture anchoring device described herein can be used in combination with multiple sutures or a single suture in various surgical procedures by surgeons to fixate sutures in the surgery. The standard suturing procedure for tissue approximation, prosthetic fixation or the like, is performed until the step of the procedure at which knot tying would typically commence. At this point, the knot tying steps are replaced with the steps for employing the suture anchoring device described herein. As illustrated in FIGS. 3a to 3d, suture anchoring device 10 is used to secure suture 63. For example, first, tension is applied to suture 63 to place the suture into a taut state. Suture anchoring device 10 is then brought into contact with suture 63 such that the suture passes through first opening 24 on first retaining member 20. Maintaining suture 63 within first opening 24, suture anchoring device 10 is maneuvered to the sutured incision 82 on wound site 80 on the tissue surface. As shown in FIG. 3b, suture 63 is then wrapped around coupler 40 by introducing the suture into space 41 between the second surface 22 and third surface 31 of the first and second retaining members and revolving the suture around the coupler 40 at least one time while maintaining the suture in a taut state. Introduction of suture 63 into space 41 may be facilitated by guiding the suture circumferentially away from the fifth surface 34 and circumferentially towards the sixth surface 35. Following the wrapping steps, while still maintaining the suture 63 in a taut state, the portion of the excess suture 64 immediately adjacent to the wrapped portion 65 of suture 63 is placed within the holding means comprised of second opening 36 in the second retaining member 30, as shown in FIG. 3c. Following placement of suture 63 into the holding means, excess suture may be trimmed. The purpose of this holding means is merely to prevent suture 63 from unwrapping from around coupler 40 over time. This holding means does not resist the tendency of the suture 63 to slacken due to resilient forces of the wound site. Instead, the resilient forces of the wound site are counteracted by the internal friction within the suture anchoring device. This friction is created within the wrapped portion 65 of suture 63, at the interface of wrapped portion 65 with coupler 40, and at the interface of the second surface 22 and third surface 31 with suture 63 as shown in FIG. 3d.

As discussed above, the suture anchoring device may be used manually, i.e., applied by the surgeon using hands, or with any surgical instruments (e.g. laparoscopic instruments) suitable for suture manipulation, tissue manipulation, or the like. Furthermore, a laparoscopic device that is specifically designed to automate the anchoring method may be used.

It should be understood that the invention and embodiments described herein serve to merely illustrate the various concepts and that a person skilled in the art may make many variations and modifications without departing from the spirit and scope of the present invention. All such variations and modifications are intended to be included within the scope of the invention as defined in the claims.

What is claimed is:

1. A suture anchoring device comprising:
   a first retaining member having a first surface, a second surface and a first outer edge; where the second surface lies in a first plane; the first retaining member having an opening that extends from the first outer edge to an inner point of the first retaining member;
   a second retaining member having a third surface, a fourth surface, a fifth surface, a sixth surface and a second outer edge; where the third surface lies in a second plane and the fifth surface and the sixth surface lie nominally perpendicular to the second outer edge at their lines of intersection therewith;
   a holding means positioned within the second retaining member, the holding means comprised of an opening extending from the fifth or the sixth surface to within the second retaining member; and
   a coupler having a third outer edge and a cross-sectional area taken in a plane parallel to the first plane that is smaller than the cross-sectional area of the first retaining member taken in a plane parallel to the first plane; where the coupler is positioned along a longitudinal axis of said first retaining member and said second retaining member that is substantially perpendicular to said first and second planes and located at a midpoint of a width of said first and second retaining members and joins the first retaining member to the second retaining member at the second surface and the third surface;
   wherein the second and third surfaces are parallel to each other and non-coterminous and the opening on the first retaining member extends from the first outer edge to the third outer edge of the coupler.

2. The suture anchoring device of claim 1, where the holding means opening further comprises an entrance and a rear surface and the width of the entrance is less than the width of the rear surface.

3. The suture anchoring device of claim 1, where the coupler is a cylindrical member.

4. The suture anchoring device of claim 1, where the coupler is a helical member.

5. The suture anchoring device of claim 1, where the cross-sectional area of the first retaining member taken in a plane parallel to the first plane is larger than the cross-sectional area of the second retaining member taken in a parallel plane.

6. The suture anchoring device of claim 1, where the cross-sectional area of the first retaining member taken in a plane parallel to the first plane is smaller than the cross-sectional area of the second retaining member taken in a parallel plane.

7. The suture anchoring device of claim 1, where the cross-sectional area of the first retaining member taken in a plane parallel to the first plane is substantially the same as the cross-sectional area of the second retaining member taken in a parallel plane.

8. The suture anchoring device of claim 1, where surfaces and corners are rounded.

9. A suture anchoring device comprising:
   a first retaining member having a first surface, a second surface and a first outer edge; where the second surface lies in a first plane; the first retaining member having an opening that extends from the first outer edge to an inner point of the first retaining member;
   a second retaining member having a third surface, a fourth surface, a fifth surface, a sixth surface and a second outer edge; where the third surface lies in a second plane and the fifth surface and the sixth surface lie nominally perpendicular to the second outer edge at their lines of intersection therewith;
   a holding means positioned within the second retaining member, the holding means comprised of an opening extending from the fifth or the sixth surface to within the second retaining member; and
   a coupler having a third outer edge and a cross-sectional area taken in a plane parallel to the first plane that is smaller than the cross-sectional area of the first retaining member taken in a plane parallel to the first plane; where the coupler is positioned along a longitudinal axis of said first retaining member and said second retaining member that is substantially perpendicular to said first and second planes and located at a midpoint of a width of said first and second retaining members and joins the first retaining member to the second retaining member at the second surface and the third surface;
   wherein the second and third surfaces are parallel to each other and non-coterminous and the coupler is a cylindrical member.

10. The suture anchoring device of claim 9, where the opening on the first retaining member extends from the first outer edge to the third outer edge of the coupler.

11. The suture anchoring device of claim 9, where the opening on the first retaining member extends from the second surface to the first surface.

12. The suture anchoring device of claim 9, where the cross-sectional area of the first retaining member taken in a plane parallel to the first plane is larger than the cross-sectional area of the second retaining member taken in a parallel plane.

13. The suture anchoring device of claim 9, where the cross-sectional area of the first retaining member taken in a plane parallel to the first plane is smaller than the cross-sectional area of the second retaining member taken in a parallel plane.

14. The suture anchoring device of claim 9, where the cross-sectional area of the first retaining member taken in a plane parallel to the first plane is substantially the same as the cross-sectional area of the second retaining member taken in a parallel plane.

15. The suture anchoring device of claim 9, where surfaces and corners are rounded.

16. A suture anchoring device comprising:
   a first retaining member having a first surface, a second surface and a first outer edge; where the second surface lies in a first plane; the first retaining member having an opening that extends from the first outer edge to an inner point of the first retaining member;
   a second retaining member having a third surface, a fourth surface, a fifth surface, a sixth surface and a second outer edge; where the third surface lies in a second plane and the fifth surface and the sixth surface lie nominally perpendicular to the second outer edge at their lines of intersection therewith;
   a holding means positioned within the second retaining member, the holding means comprised of an opening extending from the fifth or the sixth surface to within the second retaining member; and
   a coupler having a third outer edge and a cross-sectional area taken in a plane parallel to the first plane that is smaller than the cross-sectional area of the first retaining member taken in a plane parallel to the first plane; where the coupler is positioned along a longitudinal axis of said first retaining member and said second retaining member that is substantially perpendicular to said first and second planes and located at a midpoint of a width of said first and second retaining members and joins the first retaining member to the second retaining member at the second surface and the third surface;

wherein the second and third surfaces are parallel to each other and non-coterminous and the coupler is a helical member.

17. The suture anchoring device of claim 16, where the opening on the first retaining member extends from the first outer edge to the third outer edge of the coupler.

18. The suture anchoring device of claim 16, where the opening on the first retaining member extends from the second surface to the first surface.

19. The suture anchoring device of claim 16, where the holding means opening further comprises an entrance and a rear surface and the width of the entrance is less than the width of the rear surface.

20. The suture anchoring device of claim 16, where the cross-sectional area of the first retaining member taken in a plane parallel to the first plane is smaller than the cross-sectional area of the second retaining member taken in a parallel plane.

21. A suture anchoring device comprising:

a first retaining member having a first surface, a second surface and a first outer edge; where the second surface lies in a first plane; the first retaining member having an opening for receiving a suture that extends from the first outer edge to an inner point of the first retaining member;

a second retaining member having a third surface, a fourth surface, a fifth surface, a sixth surface and a second outer edge; where the third surface lies in a second plane and the fifth surface and the sixth surface lie nominally perpendicular to the second outer edge at their lines of intersection therewith;

a holding means for receiving a suture positioned within the second retaining member, the holding means comprised of an opening extending from the fifth or the sixth surface to within the second retaining member; and a coupler having a third outer edge for providing a winding surface for a suture and a cross-sectional area taken in a plane parallel to the first plane that is smaller than the cross-sectional area of the first retaining member taken in a plane parallel to the first plane; where the coupler is positioned along a longitudinal axis of said first retaining member and said second retaining member that is substantially perpendicular to said first and second planes and located at a midpoint of a width of said first and second retaining members and joins the first retaining member to the second retaining member at the second surface and the third surface;

wherein the second and third surfaces are parallel to each other and non-coterminous and the opening on the first retaining member extends from the first outer edge to the third outer edge of the coupler, and wherein said suture-receiving opening, holding means, and suture winding surface of said coupler provide a frictional hold for a suture.

22. The suture anchoring device of claim 21 wherein the outer edges of said first and second retaining members are substantially annular, and wherein said width corresponds to a diameter of said first and second retaining members.

* * * * *